United States Patent
Langer et al.

(10) Patent No.: US 6,933,406 B1
(45) Date of Patent: Aug. 23, 2005

(54) METHOD FOR PRODUCING 2-HALO-6-NITROBENZOIC ACIDS

(75) Inventors: Reinhard Langer, Tönisvorst (DE); Alexander Klausener, Pulheim (DE)

(73) Assignee: Bayer Aktiengesellschaft, Leverkusen (DE)

( * ) Notice: Subject to any disclaimer, the term of this patent is extended or adjusted under 35 U.S.C. 154(b) by 345 days.

(21) Appl. No.: 10/009,699

(22) PCT Filed: Jun. 6, 2000

(86) PCT No.: PCT/EP00/05168

§ 371 (c)(1),
(2), (4) Date: Dec. 7, 2001

(87) PCT Pub. No.: WO00/76951

PCT Pub. Date: Dec. 21, 2000

(30) Foreign Application Priority Data

Jun. 16, 1999 (DE) .......................... 199 27 408

(51) Int. Cl.⁷ ............................................ C07C 51/097
(52) U.S. Cl. ...................................... 562/410; 562/409
(58) Field of Search ................................. 562/410, 409

(56) References Cited

U.S. PATENT DOCUMENTS

| | | | |
|---|---|---|---|
| 2,387,341 A | * | 10/1945 | Ogilvie et al. |
| 2,407,182 A | | 9/1946 | Sievenpiper ................. 260/618 |
| 2,429,493 A | | 10/1947 | Sievenpiper et al. ........ 260/646 |
| 3,979,448 A | * | 9/1976 | Handrick et al. |
| 5,198,575 A | | 3/1993 | Hagen et al. ................ 562/410 |

FOREIGN PATENT DOCUMENTS

DE    34 09 244    9/1985

OTHER PUBLICATIONS

"Advanced Organic Chemistry" 3rd edition, John Wiley & Sons, Inc.; Jerry March, 1985, p. 1084.*

Aust J. Chem. 25, (month unavailable) 1972, pp. 639–646, B.D. Andrews, A.J. Poynton and I.D. Rae, Steric Hindrance to Hydrogen Bonding in Ortho–Substituted.

Helv. Chim. Acta. 12, (month unavailable) 1929, pp. 921–934, von Louis Gindrauz, Zur Kenntnis der Nitro–chlor–toluole.

Chem. Ber. 70, (month unavailable) 1937, pp. 1526–1536, Kurt Lehmstedt und Karl Schrader: Synthesen in der Acridonreih (XVII. Mittel. Über Acridin).

* cited by examiner

Primary Examiner—Rosalynd Keys
(74) Attorney, Agent, or Firm—Diderico van Eyl

(57) ABSTRACT

The present invention relates to a process for the preparation of 2-halo-6-nitrobenzoic acids by oxidation of 2-halo-6-nitro-benzyl alcohols, esters, ethers, or mixtures thereof with nitric acid and to the use of this process as a step in the preparation of 2-halo-6-nitrobenzoic acids from 2-halo-6-nitrotoluenes.

14 Claims, No Drawings

METHOD FOR PRODUCING 2-HALO-6-NITROBENZOIC ACIDS

The present invention relates to a process for the preparation of 2-halo-6-nitrobenzoic acids by oxidation of 2-halo-6-nitro-benzyl alcohols and/or esters and/or ethers thereof with nitric acid and to the use of this process as a key step in the preparation of 2-halo-6-nitrobenzoic acids starting from 2-halo-6-nitrotoluenes.

For the preparation of 2-halo-6-nitrobenzoic acids, only a few methods are prior art:

B. D. Andrews describes, in Aust. J. Chem. 25 (1972) p. 639–646, the hydrolysis of 2-halo-6-nitrobenzonitrile. With a yield of 38%, the hydrolysis of the 2-halo-6-nitrobenzonitrile is unsatisfactory.

EP-A-529426 and DE-A-3409244 disclose the oxidation of 2-halo-6-nitrotoluene with nitric acid. DE-A-3409244 describes the oxidation of 2-halo-6-nitrotoluene with dilute nitric acid at 220° C. and 30 bar. The conversion is incomplete, the work-up is complicated and the reactor is expensive due to the required pressure resistance. EP-A-529426 describes a pressureless method for the oxidation of 2-halo-6-nitrotoluene with nitric acid. The reaction mixture has a starting material concentration of only 7.8%, comprises for the largest part very corrosive 70% strength sulfuric acid and has to be reacted at temperatures of 175° C. Extraction with o-dichlorobenzene gives the desired acid in crystalline form in a yield of about 65%.

The oxidation of 2-halo-6-nitrobenzyl alcohols with potassium permanganate is described by Lehmstedt and Schrader in Chem. Ber. 70 (1937) p. 1526–1536. This procedure gives satisfactory yields; however, manganese dioxide is unavoidably formed, which is unfavorable for industrial realizations. Furthermore, potassium permanganate is not a cost-effective oxidizing agent. Apart from the oxidation of the alcohol, Lehmstedt and Schrader also describe its preparation starting from 2-halo-6-nitrotoluenes, with the synthesis sequence bromination, nucleophilic substitution to give the acetate, and hydrolysis. In this process, concentrations of compound to be oxidized of only about 12% are likewise achieved, which leads to low space-time yields. The aqueous mixture from which the product is obtained by crystallization comprises about 7% 2-chloro-6-nitrobenzoic acid, which is obtained with a yield of 60%, based on 2-chloro-6-nitrotoluene.

In Helv. Chim. Acta 12 (1929) p. 921–934, Gindraux describes the bromination of 2-halo-6-nitrotoluene as an approximately 50% strength solution in o-dichlorobenzene, the hydrolysis of the benzyl bromide with sodium carbonate solution and its oxidation to give the aldehyde with bichromate/sulfuric acid. The chromium-containing oxidizing agent thus does not lead to the 2-halo-6-nitrobenzoic acid, and disposal of the chromium-containing waste which forms is costly due to its toxicity.

2-Halo-6-nitrobenzoic acids are important intermediates, for example for the preparation of 6-haloanthranilic acids, which in turn are used for the preparation of pharmaceuticals, crop protection products and dyes.

It was an object of the present invention to develop a process which makes 2-halo-6-nitrobenzoic acids of high purity accessible with high space-time yields under mild reaction conditions, such that these compounds can be produced in large amounts in the most cost-effective manner possible.

We have now found a process for the preparation of 2-halo-6-nitrobenzoic acids of the formula (I),

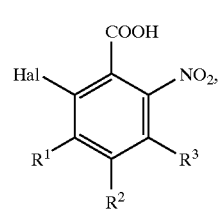

in which $R^1$, $R^2$ and $R^3$, independently of one another, are hydrogen, fluorine, chlorine, bromine, nitro or carboxyl, and Hal is fluorine, chlorine or bromine, from 2-halo-6-nitrobenzyl alcohols, esters or ethers of the formula (II)

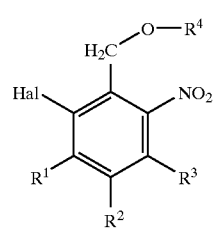

or mixtures of these compounds, where $R^1$, $R^2$, $R^3$ and Hal have the meanings given above, and $R^4$ is hydrogen, $C_1$–$C_{10}$-alkyl, $C_1$–$C_{10}$-carbonylalkyl or 2-halo-6-nitrobenzyl,
which is characterized in that 2-halo-6-nitrobenzyl compounds of the formula (II) are heated in the presence of nitric acid to temperatures between 50 and 200° C.

In addition, the invention relates to a process for the preparation of 2-halo-6-nitrobenzoic acids of the formula (I) starting from 2-halo-6-nitrotoluenes of the formula (III)

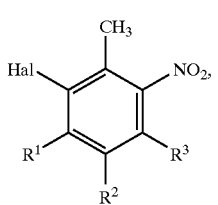

in which $R^1$, $R^2$, $R^3$ and Hal have the meanings given above, which is characterized in that a 2-halo-6-nitrotoluene of the formula (III) is converted into the corresponding 2-halo-6-nitrobenzyl bromide, followed by a nucleophilic substitution of the bromide and concluding nitric acid oxidation according to the invention.

The process according to the invention permits the preparation of 2-halo-6-nitrobenzoic acids with good yields in a simple manner with high purity. If the starting materials used are 2-halo-6-nitro-toluenes, it is not necessary to isolate the products of the bromination or of the nucleophilic substitution of the bromide in pure form, which makes it possible to carry out the process very simply.

Preferred 2-halo-6-nitrobenzyl compounds of the formula (II) are those in which $R^1$, $R^2$, $R^3$ and $R^4$ are hydrogen, and Hal is fluorine or chlorine. A particularly preferred starting material is 2-chloro-6-nitrobenzyl alcohol.

The nitric acid can, for example, comprise between 10 and 95% by weight, preferably between 35 and 90% by weight, of water. Between 1 and 10 mol of nitric acid are usually used per mole of starting material. Preference is given to the use of from 2 to 8 mol, particularly preferably from 3 to 5 mol, of nitric acid per mole of starting material.

The oxidation according to the invention is advantageously carried out at temperatures between 80° C. and 180° C., preferably between 100 and 160° C., particularly preferably between 130 and 150° C.

The reaction time can, for example, be 1 to 30, preferably 2 to 15, hours.

The compound of the formula (II) can be subjected to the oxidation according to the invention with or without solvent. If a compound of the formula (II) in solution is used, preference is given to adding enough solvent for the organic phase to comprise up to 75% by weight, particularly preferably up to 50% by weight, of solvent.

Examples of suitable solvents are all compounds which are difficult to oxidize and have melting points below 50° C., preferably below 10° C., and boiling points above 100° C., preferably above 150° C. Examples which may be mentioned are: nitrobenzene, 2-chloro-nitrobenzene, 1,2-dichlorobenzene, 1,3-dichlorobenzene, 1,2,4-trichlorobenzene, 1,2,3,4-tetrachlorobenzene, 1,1,2,2-tetrachloroethane, pyridine, pyrimidine, benzonitrile and mixtures of said solvents. Particular preference is given to using 1,2-dichlorobenzene.

The process according to the invention is generally carried out at pressures between 1 and 50 bar, preferably at 2 to 15 bar. However, it is also possible to carry out the reaction at atmospheric pressure.

In a preferred embodiment, the compound of the formula (II) is oxidized by initially introducing some or all of the nitric acid and heating it to the desired reaction temperature. The compound of the formula (II), optionally with the metered addition of further nitric acid, is metered in over 1 to 20, preferably over 2 to 10, hours. During this operation, the pressure in the reaction vessel is kept constant after a short initial phase. When the addition is complete, the mixture is after-stirred for 0.1 to 10, preferably 0.5 to 2, hours.

The reaction is carried out very particularly preferably in the absence of solvents. This is understood as meaning that residues of solvents of not more than 20% by weight, preferably not more than 10% by weight, particularly preferably not more than 5% by weight, are admixed with the compound of the formula (II) to be oxidized.

Optionally, oxidation catalysts, such as chromium, molybdenum, tungsten or vanadium compounds, may be present and, apart from nitric acid, small amounts of sulfuric acid. Preference is given to carrying out the oxidation exclusively with nitric acid/water mixtures.

The oxidation can also be carried out continuously, e.g. in a residence time tubular reactor.

According to the invention, 2-halo-6-nitrobenzoic acids of the formula (I) are also accessible in a multistage process starting from 2-halo-6-nitrotoluenes of the formula (III). For this, bromination is firstly carried out in a manner known per se, then the resulting bromide is nucleophilically substituted in a manner known per se and, finally, oxidation with nitric acid is carried out according to the invention.

Preferred compounds of the formula (III) are those in which $R^1$, $R^2$ and $R^3$ are hydrogen, and Hal is fluorine or chlorine. Particular preference is given to 2-chloro-6-nitrotoluene.

The bromination is preferably carried out with elemental bromine or N-bromo-succinimide.

The nucleophilic substitution of the bromide is preferably carried out by reaction with alkali metal or alkaline earth metal carbonates and/or hydrogencarbonates, by reaction with organic alkali metal or alkaline earth metal carboxylates or by reaction with alkali metal or alkaline earth metal alkoxides or hydroxides.

Preferably, the first two reaction steps (bromination, substitution of the bromide) are carried out in the presence of a solvent. It is possible to use the solvents which have already been described above. Particular preference is given to 1,2-dichlorobenzene.

These process steps are preferably carried out without intermediate isolation of the bromide and without isolation of the alcohol, ether or ester and without a solvent change, and the oxidation according to the invention follows directly. At the end of the reaction sequence, the prepared acid of the formula (I) can be obtained in high purity by crystallization.

After the bromide substitution stage, some or all of the solvent is particularly preferably separated off from the compound of the formula (II) by evaporation.

The combination of the process steps bromination, bromide substitution and oxidation with nitric acid permits, starting from 2-halo-6-nitrotoluenes of the formula (III), the preparation of 2-halo-6-nitrobenzoic acids of the formula (I) by means of a reaction sequence which is very easy to realize industrially.

The process according to the invention can, for example, be carried out as follows. A reactor fitted with stirrer, inlet pipe and condenser is charged with a solvent, and a 2-halo-6-nitrotoluene of the formula (III) is dissolved. At temperatures between 120 and 200° C., preferably between 140 and 180° C., elemental bromine is introduced via the tube. When bromination is complete, the system is cooled to 20 to 50° C., and nitrogen is used to expel dissolved HBr and bromine residues. An aqueous sodium carbonate solution is then pumped in and the reaction mixture is heated, under autogenous pressure, to 80 to 160° C., preferably to 90 to 130° C. When bromine substitution is complete, the system is cooled to 20 to 80° C. and the aqueous phase is separated off from the organic phase. At 80 to 160° C., preferably 90 to 140° C., 65% strength by weight aqueous nitric acid is pumped into the organic phase, and the mixture is stirred until oxidation is complete. During this operation, water which forms can be distilled off, meaning that the acid concentration remains constant. When oxidation is complete, the nitric acid is distilled off, so that only organic phase remains in the reactor, and the 2-halo-6-nitrobenzoic acid of the formula (I) is crystallized by cooling the solution to about 25° C.

The crystallization is completed by further cooling to approximately 0° C., and the crystals are separated off by filtration. After-washing with a small amount of pure cold solvent gives pure 2-halo-6-nitrobenzoic acid of the formula (I) with yields which are generally between 50% and 80%, based on the 2-halo-6-nitrotoluene of the formula (III) used.

Preference is given to carrying out the oxidation of the alcohol inversely, i.e. the nitric acid is initially introduced and the alcohol is pumped in. The alcohol is advantageously freed from solvent prior to the addition.

By carrying out the reaction inversely, it is possible to obtain yields of up to 95% of theory for the oxidation according to the invention. Moreover, carrying out the reaction inversely is very safe on an industrial scale.

The process according to the invention for the preparation of 2-chloro-6-nitrobenzoic acid has proven particularly successful.

The process according to the invention for the preparation of 2-halo-6-nitrobenzoic acids is illustrated in more detail by reference to the examples below, without limiting it in any way to these examples.

EXAMPLES

Unless stated otherwise, the percentages are given in mol %. Yield data is based on 2-chloro-6-nitro-toluene used.

Example 1

Bromination of 2-chloro-6-nitrotoluene 400 g of 2-chloro-6-nitrotoluene were dissolved in 369 g of 1,2-dichlorobenzene and heated to 165° C. under nitrogen. After the reaction temperature had been reached, 447 g of bromine were metered in over the course of 6 hours, and the mixture was after-stirred for half an hour. The resulting stream of HBr was passed through a condenser in order to precipitate out entrained bromine and return it to the reaction.

Following bromination, the mixture was cooled to 100° C., and HBr and bromine residues were expelled using nitrogen.

Analysis of the mixture revealed 0.47 mol % of unreacted 2-chloro-6-nitrotoluene and 99.4 mol % of 2-chloro-6-nitrobenzyl bromide.

Example 2
Preparation of 2-chloro-6-nitrobenzyl alcohol

The reaction mixture from example 1 was cooled to 40° C., and 120 mol % (based on 2-chloro-6-nitrotoluene used) of a 20% strength by weight aqueous sodium carbonate solution were added. The well-stirred mixture was heated to 120° C. and stirred for 6 hours at this temperature, during which a pressure of 5–6 bar resulted.

The reaction mixture was cooled to 40° C., and the aqueous phase was separated from the organic phase.

Analysis of the organic phase revealed 0.6 mol % of unreacted 2-chloro-6-nitrotoluene, 0.1 mol % of unreacted 2-chloro-6-nitrobenzyl bromide and 98 mol % of 2-chloro-6-nitrobenzyl alcohol.

Example 3
Oxidation of 2-chloro-6-nitrobenzyl alcohol

The organic phase from example 2 was heated to 140° C. and, over the course of 4 hours, 220 mol % (based on 2-chloro-6-nitrotoluene used) of 65% strength by weight nitric acid were added, and the mixture was after-stirred for 2 hours. During this operation, an approximately 9% strength by weight aqueous nitric acid distilled off, and nitrous gases escaped. Codistilled 1,2-dichlorobenzene was returned to the batch.

Residual nitric acid/water mixture was distilled off and the reaction mixture was cooled to 0° C. over the course of 4 hours. The precipitated 2-chloro-6-nitrobenzoic acid was filtered over and washed with a small amount of cold 1,2-dichlorobenzene.

Drying gave pure 2-chloro-6-nitrobenzoic acid in 60% yield (based on 2-chloro-6-nitrotoluene).

Example 4
Inverse Oxidation of 2-chloro-6-nitrobenzyl alcohol

The organic phase from example 2 was heated to 100° C., and 1,2-dichlorobenzene was distilled off at 15 mbar over 2 hours to a residual content of 4% by weight.

400 mol % (based on 2-chloro-6-nitrotoluene used) of 65% strength by weight nitric acid were initially introduced into an autoclave and heated to 140° C. The benzyl alcohol, largely freed from the solvent, was metered in uniformly over the course of 8.5 hours. During this operation, the pressure in the autoclave was kept constant at 10 bar. Escaping nitric acid and 1,2-dichlorobenzene was not replaced. After the total amount of benzyl alcohol had been pumped in, the mixture was after-stirred for 10 minutes, cooled to 100° C. and decompressed.

Aqueous nitric acid was distilled off with a gentle vacuum, and the residue which remained was dissolved with 400 g of 1,2-dichlorobenzene.

Analysis of the mixture revealed 1.44 mol % of unreacted 2-chloro-6-nitrobenzyl alcohol, 0.26 mol % of 2-chloro-6-nitrobenzaldehyde and 90 mol % of 2-chloro-6-nitrobenzoic acid.

The mixture was cooled to 25° C. over the course of 4 hours. The precipitated 2-chloro-6-nitrobenzoic acid was filtered off and washed with a small amount of cold 1,2-dichlorobenzene. Drying gave pure 2-chloro-6-nitrobenzoic acid in 78% yield (based on 2-chloro-6-nitrotoluene used).

What is claimed is:

1. A process for the preparation of 2-halo-6-nitrobenzoic acids of formula (I)

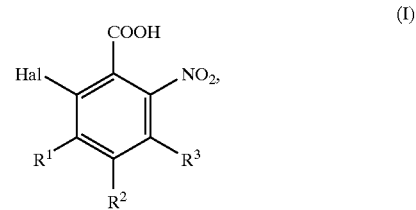

wherein $R^1$, $R^2$, and $R^3$, independently of one another, are hydrogen, fluorine, chlorine, bromine, nitro, or carboxyl, and Hal is fluorine, chlorine, or bromine, comprising heating a 2-halo-6-nitrobenzyl alcohol, ester, or ether of formula (II) or a mixture thereof,

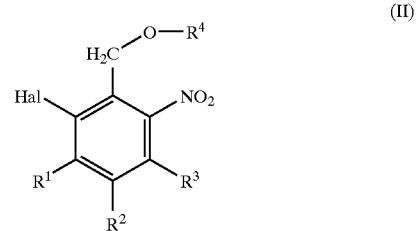

wherein $R^1$, $R^2$, $R^3$, and Hal have the meanings given above for formula (I), and $R^4$ is hydrogen, $C_1$–$C_{10}$-alkyl, $C_1$–$C_{10}$-carbonylalkyl, or 2-halo-6-nitrobenzyl, in the presence of between 1 and 10 mol, per mole of alcohol, ester, or ether of formula (II), of nitric acid comprising between 35 and 90% by weight of water at a temperature between 50 and 200° C.

2. A process according to claim 1 wherein $R^1$, $R^2$, $R^3$, and $R^4$ are hydrogen and Hal is fluorine or chlorine.

3. A process according to claim 1 wherein the 2-halo-6-nitrobenzyl compound of formula (II) is 2-chloro-6-nitrobenzyl alcohol.

4. A process according to claim 1 wherein 2 to 8 mol of nitric acid are used per mole of the 2-halo-6-nitrobenzyl alcohol, ester, or ether of formula (II).

5. A process according to claim 1 wherein some or all of the nitric acid is introduced before the 2-halo-6-nitrobenzyl alcohol, ester, or ether of formula (II) is metered in.

6. A process according to claim 1 wherein not more than 20% by weight of a solvent, based on the 2-halo-6-nitrobenzyl alcohol, ester, or ether of formula (II), is admixed with the 2-halo-6-nitrobenzyl alcohol, ester, or ether of formula (II).

7. A process for the preparation of 2-halo-6-nitrobenzoic acids of formula (I) comprising (1) converting a 2-halo-6-nitrotoluene of formula (III)

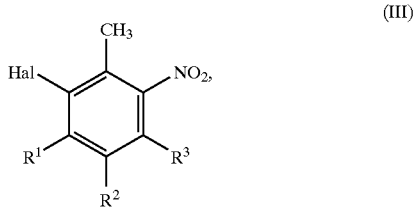

(III)

wherein
R¹, R², and R³, independently of one another, are hydrogen, fluorine, chlorine, bromine, nitro, or carboxyl, and
Hal is fluorine, chlorine or bromine,
by a bromination into the corresponding 2-halo-6-nitrobenzyl bromide, (2) carrying out a nucleophilic substitution of the 2-halo-6-nitrobenzyl bromide to form a 2-halo-6-nitrobenzyl alcohol, ester, or ether of formula (II) or a mixture thereof,

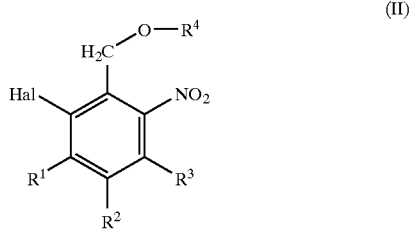

(II)

wherein
R¹, R², R³, and Hal have the meanings given above for formula (I), and
R⁴ is hydrogen, $C_1$–$C_{10}$-alkyl, $C_1$–$C_{10}$-carbonylalkyl, or 2-halo-6-nitrobenzyl, and (3) heating the 2-halo-6-nitrobenzyl alcohol, ester, or ether of formula (II) or a mixture thereof in the presence of between 1 and 10 mol, per mole of alcohol, ester, or ether of formula (II), of nitric acid comprising between 35 and 90% by weight of water at a temperature between 50 and 200° C.

8. A process according to claim 7 wherein for the 2-halo-6-nitrotoluene of formula (III) wherein R¹, R², and R³ are hydrogen and Hal is fluorine or chlorine.

9. A process according to claim 7 wherein the 2-halo-6-nitrobenzyl compound of formula (II) is 2-chloro-6-nitrobenzyl alcohol.

10. A process according to claim 7 wherein the nucleophilic substitution is carried out by reaction of the 2-halo-6-nitrobenzyl bromide with an alkali metal or alkaline earth metal carbonate and/or hydrogen carbonate, an organic alkali metal or alkaline earth metal carboxylate, or an alkali metal or alkaline earth metal alkoxide or hydroxide.

11. A process according to claim 7 wherein 2 to 8 mol of nitric acid are used per mole of the 2-halo-6-nitrobenzyl alcohol, ester, or ether of formula (II).

12. A process according to claim 7 wherein some or all of the nitric acid is introduced before the 2-halo-6-nitrobenzyl alcohol, ester, or ether of formula (II) is metered in.

13. A process according to claim 7 wherein the bromination and the nucleophilic substitution steps are carried out without isolation of the respective resulting products.

14. A process according to claim 7 wherein
(i) the bromination and nucleophilic substitution steps are each carried out in the presence of a solvent, wherein the solvents for each step are optionally the same or different,
(ii) the solvent is removed such that not more than 20% by weight of solvent, based on the 2-halo-6-nitrobenzyl alcohol, ester, or ether of formula (II), are present, and
(iii) the 2-halo-6-nitrobenzyl alcohol, ester, or ether of formula (II) is oxidized.

* * * * *